(12) United States Patent
Kong et al.

(10) Patent No.: US 12,387,850 B1
(45) Date of Patent: Aug. 12, 2025

(54) METHOD AND SYSTEM FOR RECOMMENDATION AND COMPARATIVE ANALYSIS OF ANIMAL MODEL OF NEUROLOGICAL DISEASES

(71) Applicant: Institute of Laboratory Animal Sciences, CAMS & PUMC, Beijing (CN)

(72) Inventors: Qi Kong, Beijing (CN); Chuan Qin, Beijing (CN); Yue Wu, Beijing (CN); Ling Zhang, Beijing (CN); Jue Wang, Beijing (CN); Tingting Feng, Beijing (CN); Yitong Li, Beijing (CN)

(73) Assignee: Institute of Laboratory Animal Sciences, CAMS & PUMC, Beijing (CN)

( * ) Notice: Subject to any disclaimer, the term of this patent is extended or adjusted under 35 U.S.C. 154(b) by 0 days.

(21) Appl. No.: 18/909,655

(22) Filed: Oct. 8, 2024

(51) Int. Cl.
*G16H 50/50* (2018.01)
*G16B 20/00* (2019.01)
*G16H 50/70* (2018.01)

(52) U.S. Cl.
CPC .............. *G16H 50/50* (2018.01); *G16B 20/00* (2019.02); *G16H 50/70* (2018.01)

(58) Field of Classification Search
CPC ......... G16H 50/50; G16H 50/70; G16B 20/00
See application file for complete search history.

(56) References Cited

U.S. PATENT DOCUMENTS 6,317,741 B1 * 11/2001 Burrows ............... G06F 16/328
707/999.005
12,124,966 B1 * 10/2024 Alperin .................... G06F 40/30

(Continued)

FOREIGN PATENT DOCUMENTS

| CN | 118098621 A | * | 5/2024 |
| JP | 2019063377 A | * | 4/2019 |
| NL | 2030706 B1 | * | 12/2022 |

OTHER PUBLICATIONS

Maynard et al., "A knowledge based approach to matching human neurodegenerative disease and animal models," Frontiers in Neuroinformatics www.frontiersin.org May 2013 | vol. 7 | Article 7 | doi: 10.3389/fninf.2013.00007. (Year: 2013).*

(Continued)

*Primary Examiner* — Jonathon A. Szumny
(74) *Attorney, Agent, or Firm* — Chiesa Shahinian & Giantomasi PC

(57) ABSTRACT

Provided is a method and system for recommendation and comparative analysis of an animal model of neurological diseases, and relates to the field of data analysis technology. The method includes obtaining a plurality of pieces of related literature on animal models of neurological diseases; extracting, for each piece of related literature on animal models of neurological diseases, information from the related literature on animal models of neurological diseases to obtain literature information of the related literature on animal models of neurological diseases; preprocessing the literature information to obtain phenotypes and application data corresponding to the related literature on animal models of neurological diseases, constructing an animal model database based on application data corresponding to all the related literature on animal models of neurological diseases, and developing a comparative analysis function; and determining a recommended model based on a user input instruction and the animal model database.

7 Claims, 14 Drawing Sheets

(56) References Cited

U.S. PATENT DOCUMENTS

| | | | | |
|---|---|---|---|---|
| 2006/0004732 | A1* | 1/2006 | Odom | G06F 16/951 |
| 2009/0157522 | A1* | 6/2009 | Srinivasan | G06Q 30/0601 |
| | | | | 705/26.1 |
| 2010/0057368 | A1* | 3/2010 | Afeyan | A61K 49/0004 |
| | | | | 703/11 |
| 2014/0323391 | A1* | 10/2014 | Tsalik | C12Q 1/689 |
| | | | | 514/23 |
| 2017/0104742 | A1* | 4/2017 | Chan | H04L 63/08 |
| 2018/0315227 | A1* | 11/2018 | Fujita | G06T 11/206 |
| 2019/0272890 | A1* | 9/2019 | Aliper | G16B 40/00 |
| 2019/0320628 | A1* | 10/2019 | Norwood | A61K 31/5513 |
| 2021/0052209 | A1* | 2/2021 | Hecox | A61B 5/30 |
| 2021/0156831 | A1* | 5/2021 | Yamamoto | G01N 35/00871 |
| 2022/0130493 | A1* | 4/2022 | Turner | G16H 70/40 |
| 2023/0023202 | A1* | 1/2023 | Bierner | G06F 16/245 |
| 2024/0346029 | A1* | 10/2024 | Neumann | G06F 16/24575 |

OTHER PUBLICATIONS

Flower et al., "Validity and Reliability of GraphClick and DataThief III for Data Extraction," Article in Behavior Modification • Apr. 2016; DOI: 10.1177/0145445515616105. (Year: 2016).*

Oellrich et al., "Improving Disease Gene Prioritization by Comparing the Semantic Similarity of Phenotypes in Mice with Those of Human Diseases," PLoS ONE 7(6): e38937. doi: 10.1371/journal.pone.0038937. (Year: 2012).*

Zeiss et al., "Menagerie: A text-mining tool to support animal-human translation in neurodegeneration research," PLoS ONE 14(12): e0226176. https://doi.org/10.1371/journal.pone.0226176. (Year: 2019).*

Kong et al., "LasDB: A collective database for laboratory animal strain resources," Animal Model Exp Med. 2018;1:266-271; DOI: 10.1002/ame2.12044. (Year: 2018).*

\* cited by examiner

| Model Summary | | | | | | | |
|---|---|---|---|---|---|---|---|
| Model number | Strain number | References number | Model name | Disease name | Species | Strain | Application | Affiliation |
| C0008 | S0295 | L0008 | McGill-R-Thy1-APP transgenic rat Alzheimer's disease model | Alzheimer's disease | rat | McGill-R-Thy1-APP (Tgt+/- x0050) | Drug Evaluation Research | Lenoya Institute@@https://www.leloir.org.ar/ |

Active document (A)

Please input content
- A. Model Summary
- B. Strain Information
- AB. Modeling Method
- C. Modeling of Biochemical Agent
- D. Surgical Method
- E. Model Phenotype-Behavioral
- F. Behavioral Changes Data
- G. Model Phenotype-Pathology
- H. Pathological Phenotype Data
- I. Blood Biochemistry
- J. Blood Biochemical Data
- K. Model Phenotype-Imageology
- L. Imageology Data

Fig. 3

Animal Model of Neurological Disease Database   CN EN ⊛LOGIN |REGISTER

ND-AMD serves as a resource for the scientific community, providing a comprehensive collection and helping social sharing of basic data, experimental data, phenotype data, and application data for animal models of neurological diseases, Utilizing ststistical tools for visualization and providing analytical capabilities, ND-AMD aims to display data in a visually effective manner, contributing to the advancement of dynamic, multi-scale, and multi-dimensional panoramic research paradigms

| Please enter disease | Advanced Search |

Home    Browse    Advanced Search    Analysis Tools    Data Resources

Home >>Advanced Search

Advanced Search:

| Disease type ˅ | please enter disease type name, such as Neurodegenerative Diseases, Neuropsychiatric Diseases, Cerebrovascular Diseases | + |
| Disease name ˅ | please enter Disease name name, such as Alzheimer's Disease, Parkinson's Disease, Huntington's Disease | − |
| Species ˅ | please enter Species name, such as mouse, rat, monkey, rabbit, pig. | − |
| Strain ˅ | please enter strain name, such as C57BL/6 Mouse, Wistar Rat, Sprague Dawley Rat, BLAB/c Mouse, ICR Mouse | − |
| Application ˅ | please enter Application name, such as mechanistic investigation, phenotype and symptom comparison, behavior studies | − |

(Submit)  (Reset)

Fig. 5

| Classification Navigation | Home > >Browse> >Parkinson's Disease Animal Models |
|---|---|
| Neurological Disease Animal Models |  6-OHDA Induced Swiss Albino Mouse Parkinson's Disease Model |
| Neurodegenerative Disease Animal Models | Disease: Parkinson's Disease |
| Alzheimer's Disease Animal Models | Species: mouse |
| Parkinson's Disease Animal Models | Strain: Swiss albino Mouse |
| Huntington's Disease Animal Models | Application: Phenotype and Symptom Comparison; Behavior Studies;Pathological Study |
| Amyotrophic Lateralizing Sclerosis Animal Models | Reference: Recapitulation of treatment response patterns in a novel humanized mouse model for chronic hepatitis B virusinfection, year:2017,DOI:10.1016/j.virol.2016.12. 017.PMID:28006671 |
| Other Neurodegenerative Disease Animal Models | |
| Neuropsychiatric Disease Animal Models |  6-OHDA Induced Wistar Rat Parkinson's Disease Model |
| Autoimmune Disorders of the Nervous System Animal Models | Disease:Parkinson's Disease |
| Cerebrovascular Disease Animal Models | Species:rat |
| Brain and other CNS tumors Animal Models | Strain: Wistar rat |
| Developmental Disorders of the Nervous System Animal Models | Application: Phenotype and Symptom Comparison; Behavior Studies;Pathological Study |
| Other Neuropsychiatric Disease Animal Models | Reference: Recapitulation of treatment response patterns in a novel humanized mouse model for chronic hepatitis B virus infection,year:2017,DOI:10.1016/j.virol .2016.12.017.PMID:28006671 |

Fig. 6

| | Model Summary | |
|---|---|---|
| Basic Information | Model number | C1241B |
| Strain Information | Strain number | S0124 |
| Method | Model name | 6-OHDA Induced Swiss Albino Mouse Parkinson's Disease Model |
| ⌄ Phenotype | Disease name | Parkinson's Disease |
| | Species | mouse |
| ›Behavioral Phenotypes | Modeling applications | Phenotype and Symptom Comparison; Behavior Studies;Pathological Study |
| | References number | L1241 |
| ›Pathological Phenotypes | Reference | Recapitulation of treatment response patterns in a novel humanized mouse model for chronic hepatitis B virus infection,year:2017,DOI:10.1016/j.virol.2016.12.017.PMID:28006671 |
| ⌄Biochemical Phenotypes | Affiliation | University of S?o Paulo |

🔍 Home >>Browse>>Neuropsychiatric Disease Animal Models

| Strain Information | |
|---|---|
| Strain name | Swiss albino |
| Background strain | / |
| Genes involved | / |
| Strain supplier | / |
| Strain supplier organization | / |
| Reproductive generation | / |
| Microbial quality control | SPF |
| Reproductive mode | / |

Modeling Method

| Model number | Group number | Modeling /control | Group name | Classification of |
|---|---|---|---|---|
| C1241B | C1241-002 | Experimental group | mouce experiment group | / |
| C1241B | C1241-002-01 | Model group | 6-OHDA induce mouse group | Biochemical agent |

| 1. Please select disease type. | 2. Please select disease. | 3. Please select research purpose. |
|---|---|---|
| Neurodegenerative Diseases | Alzheimer's Diseases | Mechanistic Investigation ✖ |
| | | Drug Efficacy Evaluation ✖ |

Submit

Model Frequency Analysis Results

- 3×Tg Transgenic Mouse Alzheimer's Disease Model
- 5×FAD Hemizygous Produces by Crossing with C57BL/6 or IVF Induced 5×FAD Mouse Alzheimer's Disease Model
- 5×FAD Transgenic Mouse Alzheimer's Disease Model
- APP/PS1 Transgenic Mouse Alzheimer's Disease Model
- APP Transgenic AppNL-G-F Mouse Alzheimer's Disease Model
- APP Transgenic 5×F Mouse Alzheimer's Disease Model
- APP and Tua Transgenic 3×Tg Mouse Alzheimer's Disease Model
- AD Transgenic Gittingen Minipigs Alzheimer's Disease Model
- 5×FAD/C6-KO Transgenic Mouse Alzheimer's Disease Model
- 5×FAD Transgenic PKRKO Mouse Alzheimer's Disease Model

| C0916 | 3×Tg Transgenic Mouse Alzheimer's Disease Model | DOI:10.3390/nu12113589,PMD:332384 |
| C0933A | 3×Tg Transgenic Mouse Alzheimer's Disease Model | DOI:10.4077/CJP.2015.BAD334,PMD:26 |
| C0985 | 3×Tg Transgenic Mouse Alzheimer's Disease Model | DOI:10.1016/j.cellsig.2016.08.017,PMD: |
| C0990 | 3×Tg Transgenic Mouse Alzheimer's Disease Model | DOI:10.1371/journal.pone.0080355,PM |
| C0910 | 5×FAD Transgenic Mouse Alzheimer's Disease Model | DOI:10.1038/s41598-020-58309-8,PMD |
| C0984 | 5×FAD Transgenic Mouse Alzheimer's Disease Model | DOI:10.1371/journal.pone.0150441,PM |

METHOD AND SYSTEM FOR RECOMMENDATION AND COMPARATIVE ANALYSIS OF ANIMAL MODEL OF NEUROLOGICAL DISEASES

TECHNICAL FIELD

The present disclosure relates to the field of data analysis technology, and in particular, to a method and system for recommendation and comparative analysis of an animal model of neurological diseases.

BACKGROUND

Focusing on the fields of animal models of neurological diseases, pathogenesis, disease diagnosis, drug treatment, disease prevention and treatment, and the like, with "big data-neurological diseases-animal models-mechanism research" as a main line, panoramic research is conducted dynamically in multiple scales and multiple dimensions and a database is established relying on the largest resource database of animal models of human diseases in China, and comparative analysis tools are customized and developed.

Neurological diseases are a type of diseases, including neurodegenerative diseases, animal models of nervous and mental diseases, nervous system autoimmune diseases, animal models of cerebrovascular diseases, brain and other central nervous system tumors and nervous system developmental disorders, and the like. So far, research has produced a large number of research data. Animal models are the first step in understanding diseases and one of the touchstones for overcoming diseases. With animal models, diseases can be scientifically understood, to find drug targets, and test drugs or vaccines. It is necessary to integrate data from animal models, applications and other levels and multiple angles, study a molecular mechanism of diseases and take effective preventive measures. Many studies have been published through existing open databases, but there is a lack of special databases related to animal models of neurological diseases to store, analyze and share model and phenotypic data and form comparative analysis.

SUMMARY

An objective of the present disclosure is to provide a method and system for recommendation and comparative analysis of an animal model of neurological diseases, to quickly and simply provide recommended models for users, and implement changes of different phenotypic indexes in different species and different diseases based on phenotypic comparative analysis.

To achieve the above objective, the present disclosure provides the following solutions.

A method for recommendation and comparative analysis of an animal model of neurological diseases includes:
  obtaining a plurality of pieces of related literature on animal models of neurological diseases by a terminal;
  extracting, for each piece of related literature on animal models of neurological diseases, information from the related literature on animal models of neurological diseases by a server to obtain literature information of the related literature on animal models of neurological diseases, the literature information including a model summary, a modeling strain, a modeling method, and phenotypic information, and the phenotypic information including clinical indexes, and behavioral, physiological and biochemical, pathological and image data;
  preprocessing the literature information by the server to obtain phenotypes and application data corresponding to the related literature on animal models of neurological diseases, and constructing an animal model database based on phenotypes and application data corresponding to all the related literature on animal models of neurological diseases;
  determining a recommended model by the server based on a user input instruction and the animal model database, the recommended model being configured to optimize an experimental process of drug testing for neurological diseases, the user input instruction including a disease type, a disease name, and a use, and the recommended model including the application data corresponding to the related literature on animal models of neurological diseases; and
  performing comparative analysis on the phenotypes corresponding to the related literature on animal models of neurological diseases by the server based on a user input phenotype instruction to obtain a comparative analysis result, the comparative analysis result being used to optimize the experimental process of drug testing for neurological diseases, and the user input phenotype instruction being a plurality of phenotypic types required by a user.

A system for recommendation and comparative analysis of an animal model of neurological diseases includes: a terminal and a server, where
  the terminal is configured to obtain a plurality of pieces of related literature on animal models of neurological diseases;
  the server includes an information extraction module, an animal model database construction module, a model recommendation module, and a comparative analysis module;
  the information extraction module is configured to extract, for each piece of related literature on animal models of neurological diseases, information from the related literature on animal models of neurological diseases to obtain literature information of the related literature on animal models of neurological diseases, the literature information including a model summary, a modeling strain, a modeling method, and phenotypic information, and the phenotypic information including clinical indexes, and behavioral, physiological and biochemical, pathological and image data;
  the animal model database construction module is configured to preprocess the literature information to obtain phenotypes and application data corresponding to the related literature on animal models of neurological diseases, and construct an animal model database based on phenotypes and application data corresponding to all the related literature on animal models of neurological diseases;
  the model recommendation module is configured to determine a recommended model based on a user input instruction and the animal model database, the user input instruction including a disease type, a disease name, and a use, and the recommended model including the application data corresponding to the related literature on animal models of neurological diseases; and
  the comparative analysis module is configured to perform comparative analysis on the phenotypes corresponding to the related literature on animal models of neurological diseases based on a user input phenotype instruction to obtain a comparative analysis result, the user input phenotype instruction being a plurality of phenotypic types required by a user.

According to the specific embodiments of the present disclosure, the present disclosure has the following technical effects. The present disclosure discloses a method and system for recommendation and comparative analysis of an animal model of neurological diseases. A plurality of pieces of related literature on animal models of neurological diseases are obtained by a terminal. For each piece of related literature on animal models of neurological diseases, information is extracted from the related literature on animal models of neurological diseases by a server to obtain literature information of the related literature on animal models of neurological diseases, the literature information including a model summary, a modeling strain, a modeling method, and phenotypic information, and the phenotypic information including clinical indexes, and behavioral, physiological and biochemical, pathological and image data. The literature information is preprocessed to obtain application data corresponding to the related literature on animal models of neurological diseases, and an animal model database is constructed based on phenotypes and application data corresponding to all the related literature on animal models of neurological diseases. A recommended model is determined based on a user input instruction and the animal model database, the user input instruction including a disease type, a disease name, and a use, and the recommended model including the application data corresponding to the related literature on animal models of neurological diseases. Comparative analysis is performed on phenotypes corresponding to related literature on animal models of neurological diseases based on a user input phenotype instruction to obtain a comparative analysis result, the user input phenotype instruction being a plurality of phenotypic types required by a user. According to the present disclosure, the recommended model can be simply and quickly provided to the user, and comparative analysis can be performed.

BRIEF DESCRIPTION OF THE DRAWINGS

To describe the technical solutions in embodiments of the present disclosure or in the prior art more clearly, the accompanying drawings required for the embodiments are briefly described below. Apparently, the accompanying drawings in the following description show merely some embodiments of the present disclosure, and those of ordinary skill in the art may still derive other accompanying drawings from these accompanying drawings without creative efforts.

FIG. 3 is a schematic diagram of a model data collection framework according to Embodiment 1 of the present disclosure;

FIG. 5 is a schematic diagram of an advanced search page of a nervous system animal model according to Embodiment 1 of the present disclosure;

FIG. 6 is a schematic diagram of a browsing page of a nervous system animal model according to Embodiment 1 of the present disclosure;

FIG. 7 is a schematic diagram of a detail page of a nervous system animal model database according to Embodiment 1 of the present disclosure;

FIG. 11 is a schematic diagram showing clinical scores of different species according to Embodiment 1 of the present disclosure;

FIG. 13 is a schematic diagram showing a model recommendation result according to Embodiment 1 of the present disclosure.

DETAILED DESCRIPTION OF THE EMBODIMENTS

The technical solutions of the embodiments of the present disclosure are clearly and completely described below with reference to the accompanying drawings in the embodiments of the present disclosure. Apparently, the described embodiments are merely some rather than all of the embodiments of the present disclosure. All other embodiments obtained by those of ordinary skill in the art based on the embodiments of the present disclosure without creative efforts shall fall within the protection scope of the present disclosure.

An objective of the present disclosure is to provide a method and system for recommendation and comparative analysis of an animal model of neurological diseases, aiming to simply and quickly provide a recommended model to a user.

In order to make the above objective, features and advantages of the present disclosure clearer and more comprehensible, the present disclosure is further described in detail below with reference to the accompanying drawings and specific implementations.

Embodiment 1

Figure 1:
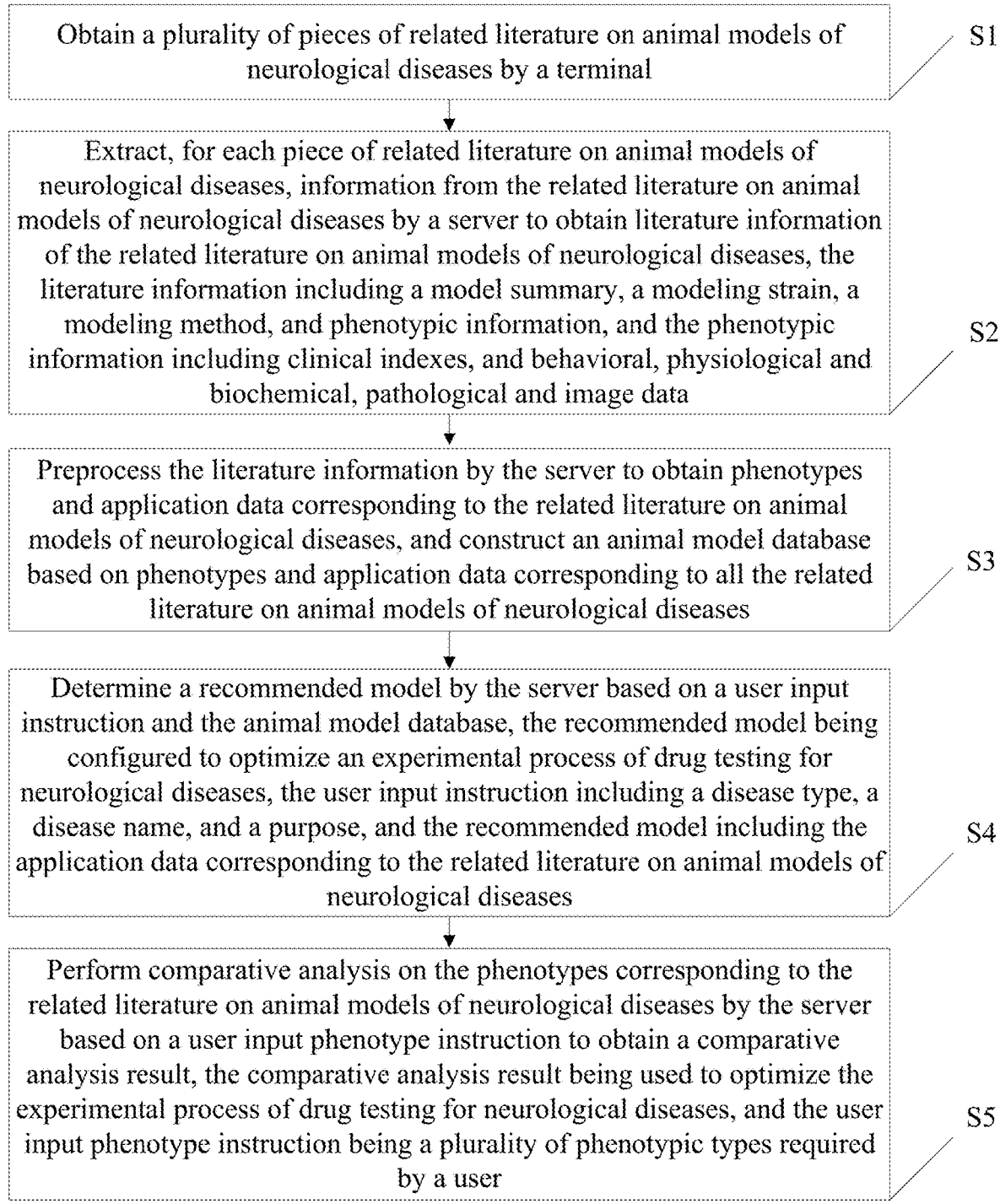
FIG. 1 is a schematic flowchart of a method for recommendation and comparative analysis of an animal model of neurological diseases according to Embodiment 1 of the present disclosure.
Figure 2:
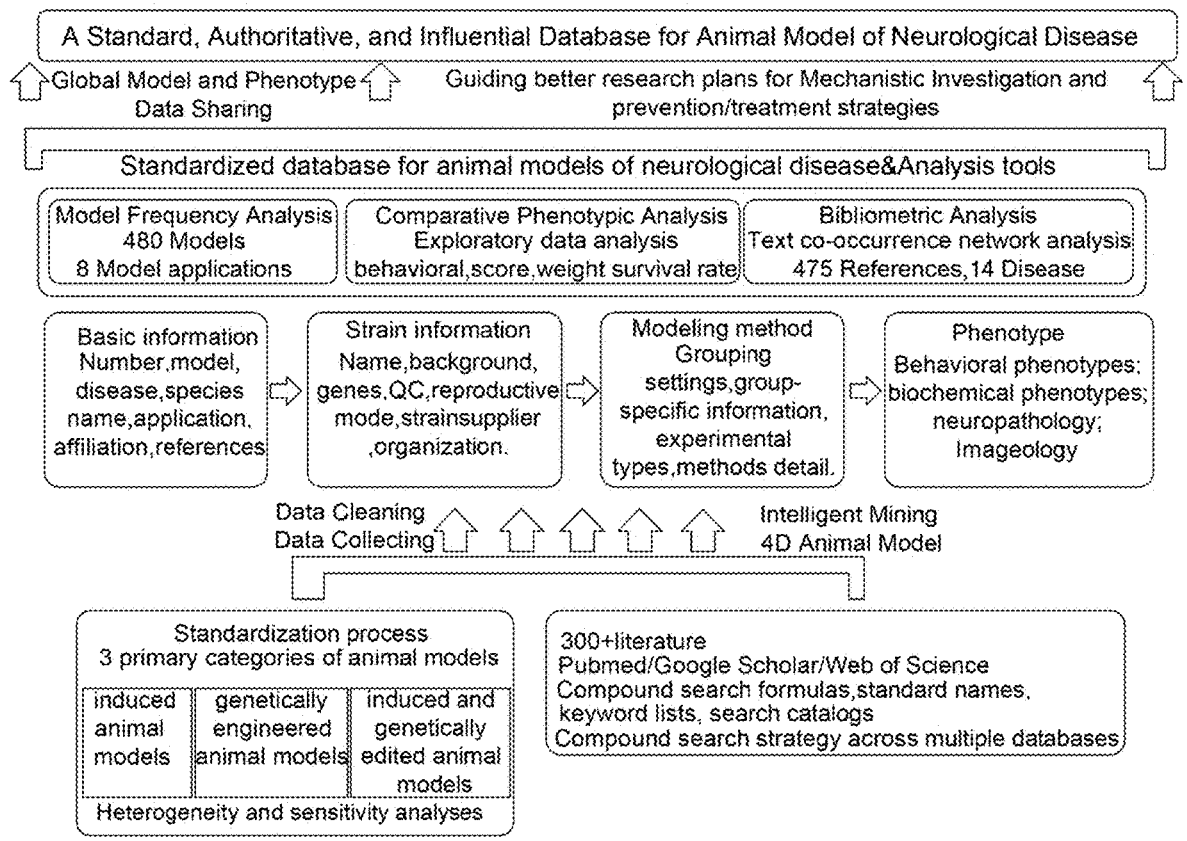
FIG. 2 is a schematic diagram of a technical route for establishing an animal model database of neurological diseases according to Embodiment 1 of the present disclosure.

As shown in FIG. 1 and FIG. 2, a method for recommendation and comparative analysis of an animal model of neurological diseases in this embodiment includes the following steps.

S1: Obtain a plurality of pieces of related literature on animal models of neurological diseases by a terminal.

S2: Extract, for each piece of related literature on animal models of neurological diseases, information from the related literature on animal models of neurological diseases by a server to obtain literature information of the related literature on animal models of neurological diseases, the literature information including a model summary, a modeling strain, a modeling method, and phenotypic information, and the phenotypic information including clinical indexes, and behavioral, physiological and biochemical, pathological and image data.

S3: Preprocess the literature information by the server to obtain phenotypes and application data corresponding to the related literature on animal models of neurological diseases, and construct an animal model database based on phenotypes and application data corresponding to all the related literature on animal models of neurological diseases.

S4: Determine a recommended model by the server based on a user input instruction and the animal model database, the recommended model being configured to optimize an experimental process of drug testing for neurological diseases, the user input instruction including a disease type, a disease name, and a use, and the recommended model including the application data corresponding to the related literature on animal models of neurological diseases.

S5: Perform comparative analysis on the phenotypes corresponding to the related literature on animal models of neurological diseases by the server based on a user input phenotype instruction to obtain a comparative analysis result, the comparative analysis result being used to optimize the experimental process of drug testing for neurological diseases, and the user input phenotype instruction being a plurality of phenotypic types required by a user.

Obtaining a plurality of pieces of related literature on animal models of neurological diseases by means of a search strategy in step S1 specifically includes: The thorough identification of relevant papers stood as a pivotal element in meta-like-analytic endeavors, as the outcome hinges upon the selection of included studies. The comprehensive search strategy across multiple databases should become imperative to ensure robustness and reliability. Employing a comprehensive search strategy across multiple databases, such as Google Scholar, PubMed, and Web of Science, is imperative to ensure a thorough retrieval of pertinent literature. This involved utilizing compound search formulas, combining "neurological disease name" with "animal model species" as keywords, to retrieve and download literature. Additionally, standard names of neurological diseases were compiled, establishing keyword lists and search catalogs to enhance the search process. At the same time, priority was given to reviewing recent reviews with high impact factors to ensure the inclusion of influential studies. Data collection was conducted according to different disease categories, with the symbol "*" representing general retrieval for neurological diseases with synonymous terms.

Inclusion criteria were established to ensure the selection of high-quality literature. This included criteria such as clear documentation of neurological animal models with transparent animal backgrounds, reliable modeling methods, and experimental designs capable of fully testing the reliability and validity of models. Furthermore, literature containing phenotype information, focusing on the similarity and reproducibility of human diseases, was prioritized.

A directory of retrieved and qualified literature was compiled, listing complete and unabridged literature titles along with PDF links for accessibility. Each entry indicated whether the literature was successfully downloaded ("Y") or not ("N"). All downloaded literature (in PDF format) was ultimately gathered by a designated collector, with proper data backup procedures implemented to ensure data integrity and security. To ensure data integrity and security, proper backup procedures were implemented. The literature database was systematically managed with regular updates, link verification, and periodic reviews to ensure all relevant literature was included and accessible, which facilitated efficient retrieval and use of the literature for data analysis and research. A nervous system animal model is collected, with disease types covering the following types: 1. Neurodegenerative diseases, such as Alzheimer's disease (AD)/Parkinson's disease (PD)/Hodgkin's disease (HD)/amyotrophic lateral sclerosis (ALS); 2. Cerebrovascular diseases, such as stroke; 3. Mental disorders, such as anxiety/depression/bipolar disorder/schizophrenia. 4. Infective neurological disorders, such as Japanese encephalitis/meningitis/tuberculous encephalitis/human immunodeficiency virus (HIV)/syphilis/herpes/prion disease/rabies, and other microbial/parasitic infections; 5. Brain and other central nervous system (CNS) tumors, such as meningioma/glioma/metastasis; 6. Developmental disorders of the nervous system, such as autism; 7. Epilepsy; 8. Autoimmune disorders of the nervous system, such as myasthenia gravis, multiple sclerosis, and Guillain-Barre syndrome; and 9. Others: peripheral nervous system disease, such as peripheral neuropathy caused by trigeminal neuralgia/sciatica/diabetes/alcoholism; and nervous system injury such as traumatic spinal cord injury and addiction.

Data collection: the related literature on animal models for neurological diseases that meet the above requirements (a search strategy and 9 disease types) are downloaded, and a digital object unique identifier (DOI) and a PubMed unique identifier (PMID) of each literature are recorded at the same time, so as to implement a function of external link of the literature in the database. A data collection table and acquisition specifications are made, and collected information such as laboratory animal information, an experimental method, a detection index, and evaluation is entered into the data collection table.

Extracting information from the related literature on animal models of neurological diseases in step S2 specifically includes: extracting information from the related literature on animal models of neurological diseases by means of a Data Thief tool.

Specifically, Data Thief is used to extract data from source data (a web page/literature/public database), and datathief.jar (https://datathief.org/) based on Java is used to collect phenotypic data in an image. The extracted data (that is, literature information) is usually displayed on an interface of DataThief, in the form of a table or other forms. The extracted data can be checked against original data and check to make sure that the extracted data is correct. If different models appear in the same literature, such as a case that the same disease occurs to different strains of the same animal, or the same disease occurs to the same strain of the same species but there are different inducers, the models are split and recorded separately. Data collected from literature is integrated, and some fields are associated with a public database to form a standard structured database that conforms to a database of animal models of neurological diseases.

The extracted literature information may be specifically divided into four parts: a model summary, a modeling strain, a modeling method, and phenotypic information.

1) Model summary: including a model number, a disease name, species (species name), a model classification, a use, a research & development unit, and a reference. The species name may be externally linked to National Center for Biotechnology Information (NCBI) Taxonomy (https://www.ncbi.nlm.nih.gov/taxonomy/?term=), and the reference is externally linked to PubMed (https://pubmed.ncbi.nlm.nih.gov/). Specific information of the model summary is shown in FIG. 3.
2) Strain information: including a strain name, a number of generations, genes involved, microbial quality control, a cultivation year, a reproduction status, and a strain supplier.
3) Modeling method: including a model number, a group number, a number of groups, modeling/comparison, a group name (Chinese/English), a modeling method classification (biochemical induction, surgery, and genetic engineering), a modeling gender, a modeling age, a modeling weight, a modeling time, a number, culture conditions, a culture temperature, a culture humidity, a diurnal cycle, and a specific modeling method corresponding to each group. A model induced by a biochemical preparation further includes a name, position and concentration of an inducer. A surgical modeling model includes a surgical method, and a name, concentration, dose and injection site of an injectable drug.
4) Phenotypic information: including clinical indexes, and behavioral, physiological and biochemical, pathological and image data.

The data collection of animal models of neurological diseases is specifically shown in Table 1 to Table 6.

TABLE 1

Model summary

| | | |
|---|---|---|
| 1.1 | ID ● | Resource number and serial number generated by a platform |
| 1.2 | Model number ● | Fill in based on a modeling method (C—biological agent, D—gene editing, E—surgical modeling, F—behavioral change) |
| 1.3 | Disease number ● | Fill in disease numbers corresponding to literature (01—AD Alzheimer's disease, 02—PD Parkinson's disease, 03—HD Huntington's disease) |
| 1.4 | Strain number ● | S + four-digit number, such as S0001 (note: a literature may have multiple strains) |
| 1.5 | Literature number ● | L-Serial number of collected literature resources by the platform |
| 1.6 | Modeling application ● | Mechanism research, phenotype and symptom comparison, drug efficacy research, vaccine prevention, behavioral research, and gene function research |
| 1.7 | Chinese name of resource ● | Chinese name of an animal model of infectious diseases, naming method: disease name + modeling method + modeling animal |
| 1.8 | English name of resource ● | Naming order the same as the Chinese name |
| 1.9 | Model classification ● | Scientific research model and business model |
| 1.10 | Accession number ● | BC-Serial number the same as the literature number |

TABLE 2

Modeling strain

| | | |
|---|---|---|
| 2.1 | Strain number ● | S-Serial number the same as ID |
| 2.2 | Chinese name ● | Chinese name of modeling animal |
| 2.3 | Name in foreign language ● | Name in foreign language recognized at home and abroad, in English herein |
| 2.4 | Latin name ● | Latin name of modeling animal |
| 2.5 | Kingdom ● | Kingdom name of modeling animal germplasm resources in animal taxonomy |
| 2.6 | Phylum ● | Phylum name of modeling animal germplasm resources in animal taxonomy |
| 2.7 | Class ● | Class name of modeling animal germplasm resources in animal taxonomy |
| 2.8 | Order ● | Order name of modeling animal germplasm resources in animal taxonomy |
| 2.9 | Family ● | Family name of modeling animal germplasm resources in animal taxonomy |
| 2.10 | Genus ● | Genus name (Latin, first letter capitalized in italics) of modeling animal germplasm resources in animal taxonomy |
| 2.11 | Species and subspecies ● | Species name or subspecies name (Latin, first letter capitalized in italics) of laboratory animal germplasm resources in animal taxonomy |
| 2.12 | Strain name | Animal names named according to genetic classification and standard nomenclature |
| 2.13 | Strain type | Type of modeling species strain |
| 2.14 | Strain supplier | Place where the animal is preserved (name and country of the institution) before the introduction of a preservation unit |
| 2.15 | Related substrain | Substrain of modeling animal strain |
| 2.16 | Cultivation year | Year when the variety and strains were successfully cultivated |
| 2.17 | Number of generations (min) | It refers to the number of reproductive generations of laboratory animals, including the number of generations before introduction into a resource library + the number of generations after the introduction into the resource library. If the number of generation before the introduction into the resource library is unknown, it may be expressed as "?". The time of the number of generations is indicated in parentheses after the number of generations. |
| 2.18 | Microbial quality control level | Conventional (CV), clean (CL), specific pathogen free (SPF), germ free (GF), and gnotobiotic (GN) |
| 2.19 | Reproduction status | Reproduction status of each litter of modeling animals |

TABLE 3

| | Biological agents | |
|---|---|---|
| 3.1 | Model number ● | Fill in based on a modeling method, for example: C0001 |
| 3.2 | Group number ● | Subdivide the groups under the model number |
| 3.3 | Modeling control ● | Select this group for modeling/experimental control |
| 3.4 | Chinese name of group ● | Modeling method + animals + modeling factors |
| 3.5 | English name of group ● | According to the above format order |
| 3.6 | Specific method | Fill in a specific modeling method (descriptive text) |
| 3.7 | Injection position | Modeling injection position |
| 3.8 | Specific injection area | Specific area of modeling injection |
| 3.9 | Modeling factors | Modeling factors during modeling |
| 3.10 | Modeling dose (min) | Minimum modeling dose of injection of modeling animals participating in the experiment |
| 3.11 | Modeling dose (max) | Maximum modeling dose of injection of modeling animals participating in the experiment |
| 3.12 | Modeling gender | Gender of modeling animals: male, female, and all |
| 3.13 | Number of groups (m) | Number of male modeling animals participating in the experiment |
| 3.14 | Number of groups (F) | Number of female modeling animals participating in the experiment |
| 3.15 | Number of groups (A) | The number of all modeling animals participating in the experiment (when no specific gender is mentioned in literature resources) |
| 3.16 | Factor dose (MIN) | Minimum factor dose of injection of modeling animals participating in the experiment |
| 3.17 | Factor dose (MAX) | Maximum factor dose of injection of modeling animals participating in the experiment |
| 3.18 | Modeling age (MIN) | Minimum age of modeling animals participating in the experiment |
| 3.19 | Modeling age (MAX) | Maximum age of modeling animals participating in the experiment |
| 3.20 | Modeling weight (MIN) | Minimum weight of modeling animals participating in the experiment |
| 3.21 | Modeling weight (MAX) | Maximum weight of modeling animals participating in the experiment |
| 3.22 | Modeling time (MIN) | Minimum modeling time of modeling animals participating in the experiment |
| 3.23 | Modeling time (MAX) | Maximum modeling time of modeling animals participating in the experiment |
| 3.24 | Culture conditions | Culture conditions of modeling animals participating in the experiment |
| 3.25 | Culture humidity (MIN) | Minimum culture humidity |
| 3.26 | Culture humidity (MAX) | Maximum culture humidity |
| 3.27 | Humidity stage | Humidity stage of modeling animals |
| 3.28 | Diurnal cycle | Diurnal cycle of modeling |
| 3.29 | Modeling mechanism | Specific modeling mechanism |
| 3.30 | Remarks | Specific modeling method |

TABLE 4

| | Gene editing | |
|---|---|---|
| 4.1 | Model number ● | Fill in based on a modeling method, for example: C0001 |
| 4.2 | Group number ● | Subdivide the groups under the model number |
| 4.3 | Modeling control ● | Select this group for modeling/experimental control |
| 4.4 | Name of group ● | Modeling method + animals + modeling factors |
| 4.5 | Specific method | Fill in a specific modeling method (descriptive text) |
| 4.6 | Mutant genes | Mutant genes of modeling animals |
| 4.7 | Specific mutant genes | Specific mutant genes of modeling animals |
| 4.8 | Modeling gender | Gender of modeling animals: male, female, and all |
| 4.9 | Number of groups (m) | Number of male modeling animals participating in the experiment |
| 4.10 | Number of groups (F) | Number of female modeling animals participating in the experiment |
| 4.11 | Number of groups (A) | The number of all modeling animals participating in the experiment (when no specific gender is mentioned in literature resources) |
| 4.12 | Modeling age (MIN) | Minimum age of modeling animals participating in the experiment |

TABLE 4-continued

Gene editing

| | | |
|---|---|---|
| 4.13 | Modeling age (MAX) | Maximum age of modeling animals participating in the experiment |
| 4.14 | Modeling weight (MIN) | Minimum weight of modeling animals participating in the experiment |
| 4.15 | Modeling weight (MAX) | Maximum weight of modeling animals participating in the experiment |
| 4.16 | Modeling time (MIN) | Minimum modeling time of modeling animals participating in the experiment |
| 4.17 | Modeling time (MAX) | Maximum modeling time of modeling animals participating in the experiment |
| 4.18 | Culture conditions | Culture conditions of modeling animals participating in the experiment |
| 4.19 | Culture humidity (MIN) | Minimum culture humidity |
| 4.20 | Culture humidity (MAX) | Maximum culture humidity |
| 4.21 | Humidity stage | Humidity stage of modeling animals |
| 4.22 | Culture temperature (MIN) | Minimum culture temperature |
| 4.23 | Culture temperature (MAX) | Maximum culture temperature |
| 4.24 | Phase temperature | Phase temperature for modeling animals |
| 4.25 | Diurnal cycle | Diurnal cycle of modeling |
| 4.26 | Modeling mechanism | Specific modeling mechanism |
| 4.27 | Remarks | Specific modeling method |

TABLE 5

Surgical modeling

| | | |
|---|---|---|
| 5.1 | Model number ● | Fill in based on a modeling method, for example: C0001 |
| 5.2 | Group number ● | Subdivide the groups under the model number |
| 5.3 | Modeling control ● | Select this group for modeling/experimental control |
| 5.4 | Chinese name of group ● | Modeling method + animals + modeling factors |
| 5.5 | English name of group ● | According to the above format order |
| 5.6 | Surgical method | Surgical method for modeling animals |
| 5.7 | Surgical position | Surgical position of modeling animals |
| 5.8 | Injectable drug | Drug injected into modeling animals |
| 5.9 | Drug concentration | concentration of the drug injected |
| 5.10 | Drug dose | Dose of the drug injected |
| 5.11 | Injection site | Injection site for modeling animals |
| 5.12 | Injection age | Injection age of modeling animals |
| 5.13 | Modeling gender | Gender of modeling animals: male, female, and all |
| 5.14 | Number of groups (m) | Number of male modeling animals participating in the experiment |
| 5.15 | Number of groups (F) | Number of female modeling animals participating in the experiment |
| 5.16 | Number of groups (A) | The number of all modeling animals participating in the experiment (when no specific gender is mentioned in literature resources) |
| 5.17 | Modeling age (MIN) | Minimum age of modeling animals participating in the experiment |
| 5.18 | Modeling age (MAX) | Maximum age of modeling animals participating in the experiment |
| 5.19 | Modeling weight (MIN) | Minimum weight of modeling animals participating in the experiment |
| 5.20 | Modeling weight (MAX) | Maximum weight of modeling animals participating in the experiment |
| 5.21 | Modeling time (MIN) | Minimum modeling time of modeling animals participating in the experiment |
| 5.22 | Modeling time (MAX) | Maximum modeling time of modeling animals participating in the experiment |
| 5.23 | Culture conditions | Culture conditions of modeling animals participating in the experiment |
| 5.24 | Culture humidity (MIN) | Minimum culture humidity |
| 5.25 | Culture humidity (MAX) | Maximum culture humidity |
| 5.26 | Humidity stage | Humidity stage of modeling animals |
| 5.27 | Culture temperature (MIN) | Minimum culture temperature |

TABLE 5-continued

| | | Surgical modeling |
|---|---|---|
| 5.28 | Culture temperature (MAX) | Maximum culture temperature |
| 5.29 | Phase temperature | Phase temperature for modeling animals |
| 5.30 | Diurnal cycle | Diurnal cycle of modeling |
| 5.31 | Modeling mechanism | Specific modeling mechanism |
| 5.32 | Remarks | Specific modeling method |

TABLE 6

| | | Behavioral changes |
|---|---|---|
| 6.1 | Model number ● | Fill in based on a modeling method, for example: C0001 |
| 6.2 | Group number ● | Subdivide the groups under the model number |
| 6.3 | Modeling control ● | Select this group for modeling/experimental control |
| 6.4 | Chinese name of group ● | Modeling method + animals + modeling factors |
| 6.5 | English name of group ● | According to the above format order |
| 6.6 | Specific method | Specific modeling method |
| 6.7 | Modeling gender | Gender of modeling animals: male, female, and all |
| 6.8 | Number of groups (m) | Number of male modeling animals participating in the experiment |
| 6.9 | Number of groups (F) | Number of female modeling animals participating in the experiment |
| 6.10 | Number of groups (A) | The number of all modeling animals participating in the experiment (when no specific gender is mentioned in literature resources) |
| 6.11 | Modeling age (MIN) | Minimum age of modeling animals participating in the experiment |
| 6.12 | Modeling age (MAX) | Maximum age of modeling animals participating in the experiment |
| 6.13 | Modeling weight (MIN) | Minimum weight of modeling animals participating in the experiment |
| 6.14 | Modeling weight (MAX) | Maximum weight of modeling animals participating in the experiment |
| 6.15 | Modeling time (MIN) | Minimum modeling time of modeling animals participating in the experiment |
| 6.16 | Modeling time (MAX) | Maximum modeling time of modeling animals participating in the experiment |
| 6.17 | Culture conditions | Culture conditions of modeling animals participating in the experiment |
| 6.18 | Culture humidity (MIN) | Minimum culture humidity |
| 6.19 | Culture humidity (MAX) | Maximum culture humidity |
| 6.20 | Humidity stage | Humidity stage of modeling animals |
| 6.21 | Culture temperature (MIN) | Minimum culture temperature |
| 6.22 | Culture temperature (MAX) | Maximum culture temperature |
| 6.23 | Phase temperature | Phase temperature for modeling animals |
| 6.24 | Diurnal cycle | Diurnal cycle of modeling |
| 6.25 | Modeling mechanism | Specific modeling mechanism |
| 6.26 | Remarks | Specific modeling method |

The preprocessing in step S3 includes: type conversion, deletion of duplicate lines, and missing value handling.

To ensure the consistency and robustness of the study results, both heterogeneity and sensitivity analyses were performed on the processed phenotypic data.

Heterogeneity assessment was pivotal in determining the consistency across study results. Each set of phenotypic data underwent rigorous testing to evaluate the null hypothesis, aiming to discern if primary study outcomes significantly differed. This evaluation encompassed both Cochran's Q test and the $I^2$ statistic. Cochran's Q test assesses if observed differences among study results are due to chance, but its accuracy may decrease with fewer studies. To supplement this, the $I^2$ statistic quantifies the proportion of total variation across studies attributable to heterogeneity. It ranges from 0% to 100%, with values indicating low (25%), moderate (50%), and high (75%) heterogeneity ($2=100\%\times(Q-df)/Q$). The utilization of Python's library named SciPy (version 1.11.1) and its statsmodels, facilitated the computation of these heterogeneity metrics, ensuring the precision and accuracy of the analysis.

Sensitivity analysis was then executed to gauge the robustness of the overall findings. This entailed systematically varying key parameters and re-evaluating the outcomes to discern any notable changes. Sensitivity analysis operates on the principle of discerning how alterations in independent variables influence a particular dependent variable under a predetermined set of assumptions. In this context, the analysis involved excluding individual studies or subsets of data to observe their impact on the overall effect size and heterogeneity metrics. By employing Pandas (version 1.5.3) in Python, diverse scenarios were simulated through the modification of input parameters, followed by re-execution of the analyses. Subsequently, the resultant outcomes were meticulously compared against the original findings to ascertain any discrepancies or variations, thereby affirming the stability and reliability of the conclusions drawn.

Based on the above preprocessing process, phenotypic data corresponding to related literature on animal models of neurological diseases, that is, preprocessed data information, can be obtained. In this embodiment, phenotypes and application data of 480 animal models of neurological diseases and related models are integrated.

A process of constructing a database is described below, and the construction of the database is specifically as follows: HTML5/CSS/JavaScript were utilized to construct the basic structure, style, and interactive functionalities of the web. jQuery 1.3, serving as a supporting tool, employed primarily for user interactions. Java 1.7 and Python 2.7 were used for handling the website's business logic and data transmission. The backend adopted the Enterprise Java Beans framework, with JBoss 6.0 serving as the middleware, and a relational database MySQL (v5.7) employed for storing and managing structured data. Built static file server using Node.js (v18.18). Nginx was implemented for implement load balancing and reverse proxy. HTTPS and SSL/TLS were utilized to ensure the security of data transmission. The system featured openness, ease of operation, user-friendly interface, reliability, and security, providing users with a unified and friendly operating interface. It was a bilingual version with English and Chinese switching options, and is freely accessible to the public.

After the animal model database is constructed, the method further includes: visually displaying data in the animal model database.

Figure 4:
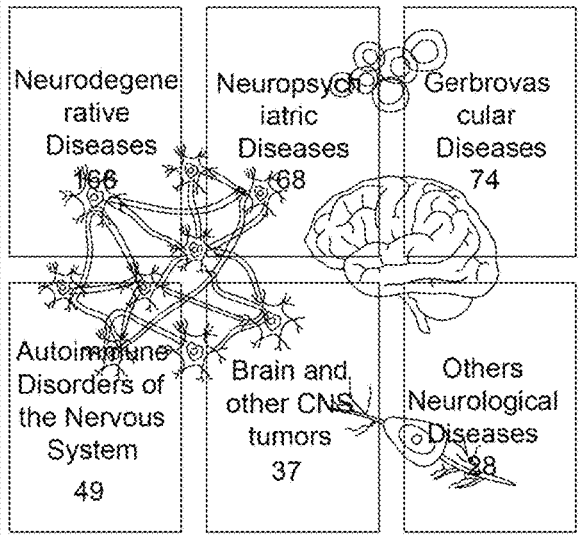
FIG. 4 is a schematic diagram of a homepage of a nervous system animal model database according to Embodiment 1 of the present disclosure.
Figure 8:
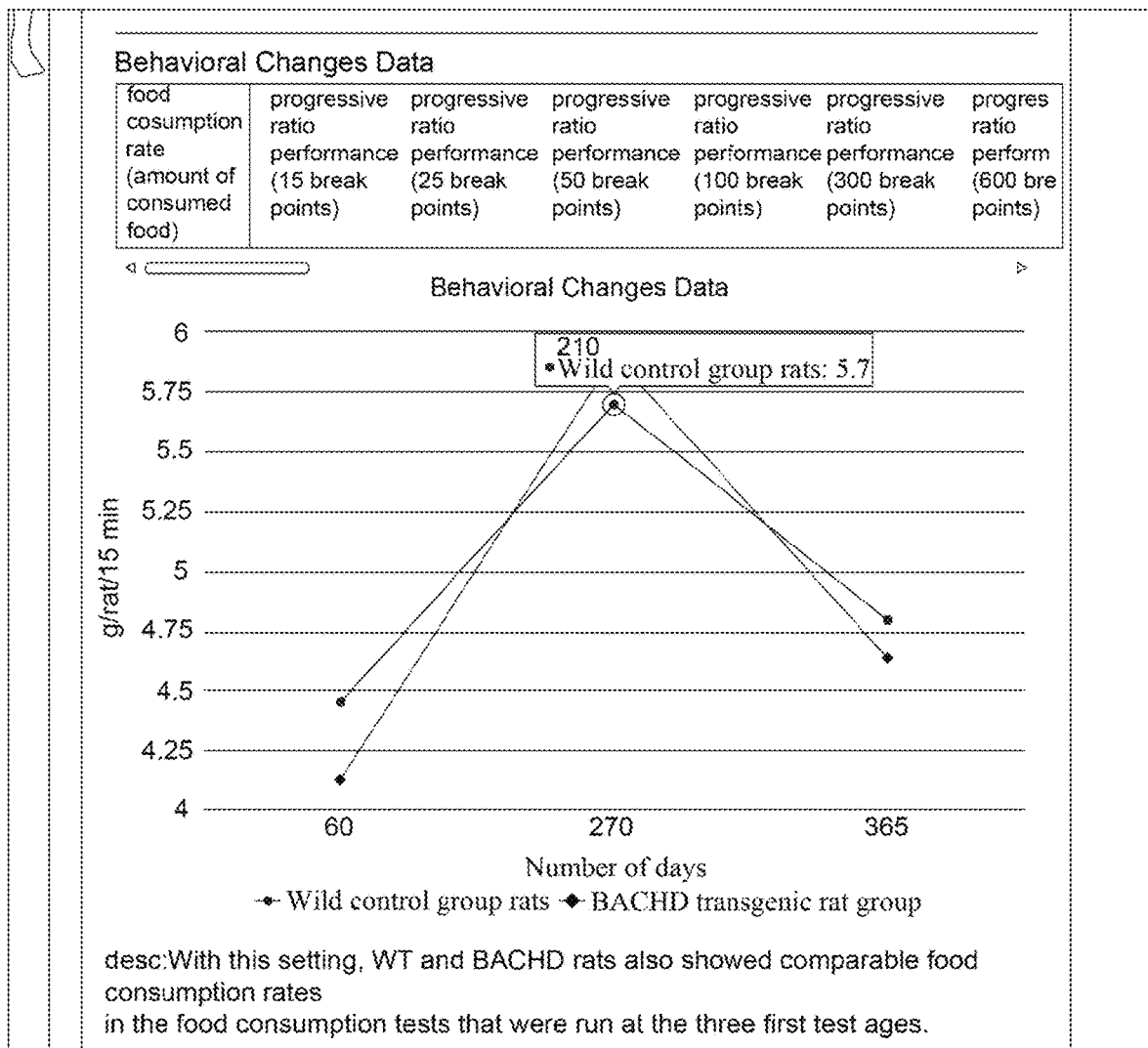
FIG. 8 is a schematic diagram of an interactive display page of phenotypic data according to Embodiment 1 of the present disclosure.
Figure 9:
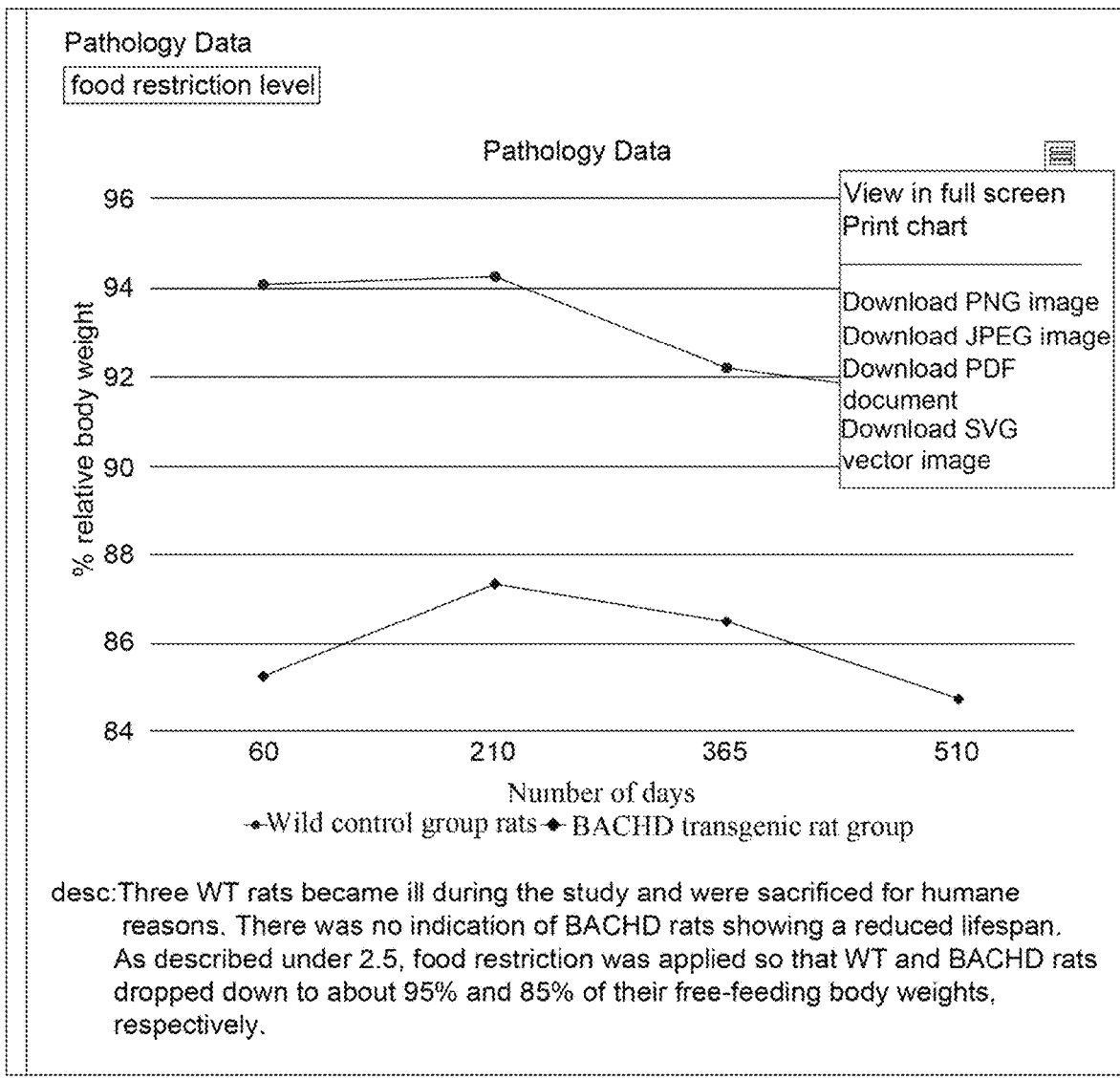
FIG. 9 is a schematic diagram of an exportable page of a visual image according to Embodiment 1 of the present disclosure.

Browsing and visualization of animal model data: according to two categories of models and model applications, animal models and animal model evaluation drug experiments and mechanism experiments are recorded and displayed. A global search and advanced search mechanism is established, and fields such as species name, strain name, disease name, application and model classification are used to query, filter and display different animal models and model application data. An advanced search function can combine multiple fields for detailed positioning. Search results skip to a browsing page, and all models or experiments related to the search content are displayed in a descending order according to relevance to a searched keyword, thereby enabling for the user to quickly find models or experiments concerned. A search page of the nervous system animal model is shown in FIG. 4. An advanced search page of the nervous system animal model is shown in FIG. 5. A browsing page of the nervous system animal model is shown in FIG. 6. A detail page of the nervous system animal model is shown in FIG. 7. An interactive display page of phenotypic data is shown in FIG. 8. An exportable page of a visual image is shown in FIG. 9.

The detail page of the nervous system animal model is divided into four parts according to the model summary, the strain information, the modeling method, and the phenotypic data. Phenotypic information is displayed in the form of a combination of a visual image and text description, and is displayed in various forms such as a line chart, a histogram, and a box plot. Real-time interaction can be performed to display specific values of different groups. The visual image may be displayed in full screen or exported in a PNG, JPEG, PDF or SVG format for the user to download. There is corresponding text description information below the image. A model data set and an application data set are provided for the user to download.

Recommendation and comparative analysis of animal model of neurological diseases:

after the animal model database is constructed, the method further includes the following step. Step 5: Perform comparative analysis on the phenotypes corresponding to the related literature on animal models of neurological diseases based on a user input phenotype instruction to obtain a comparative analysis result, which specifically includes: performing comparative analysis on phenotypic data corresponding to each piece of related literature on animal models of neurological diseases in the animal model database based on the user input phenotype instruction and a sample size in the phenotypic data, to obtain a descriptive data graph and a trend line, the descriptive data graph and the trend line forming the comparative analysis result.

Specifically, the comparative analysis of phenotypic data involved meticulous classification and statistical examination based on sample sizes. For small sample sizes ($n<30$), fine subdivision data such as clinical scores and weights were compared between groups using Welch's t-test. In this context, 'n' denotes the sample size. For medium sample sizes ($30 \leq n < 100$), behavioral indicators were assessed through independent t-tests or Analysis of Variance (ANOVA), depending on the distribution of data. Python's SciPy library facilitated the computation of accurate p-values for these tests. Additionally, the polyfit function in Python's SciPy library was utilized to fit a quadratic polynomial and describe data trends.

The steps of ANOVA were rigorously followed, beginning with the formulation of null and alternative hypotheses to test for differences in means among groups. The F-statistic was computed using sample data, and p-values were calculated based on the F-statistic, number of groups, and sample size. Decision-making regarding the null hypothesis was guided by comparing the p-value to the significance level (typically 0.05), with rejection indicating significant differences in at least one group mean. Subsequently, multiple comparisons, such as Tukey's HSD test, could be performed to identify specific group differences.

Figure 10:
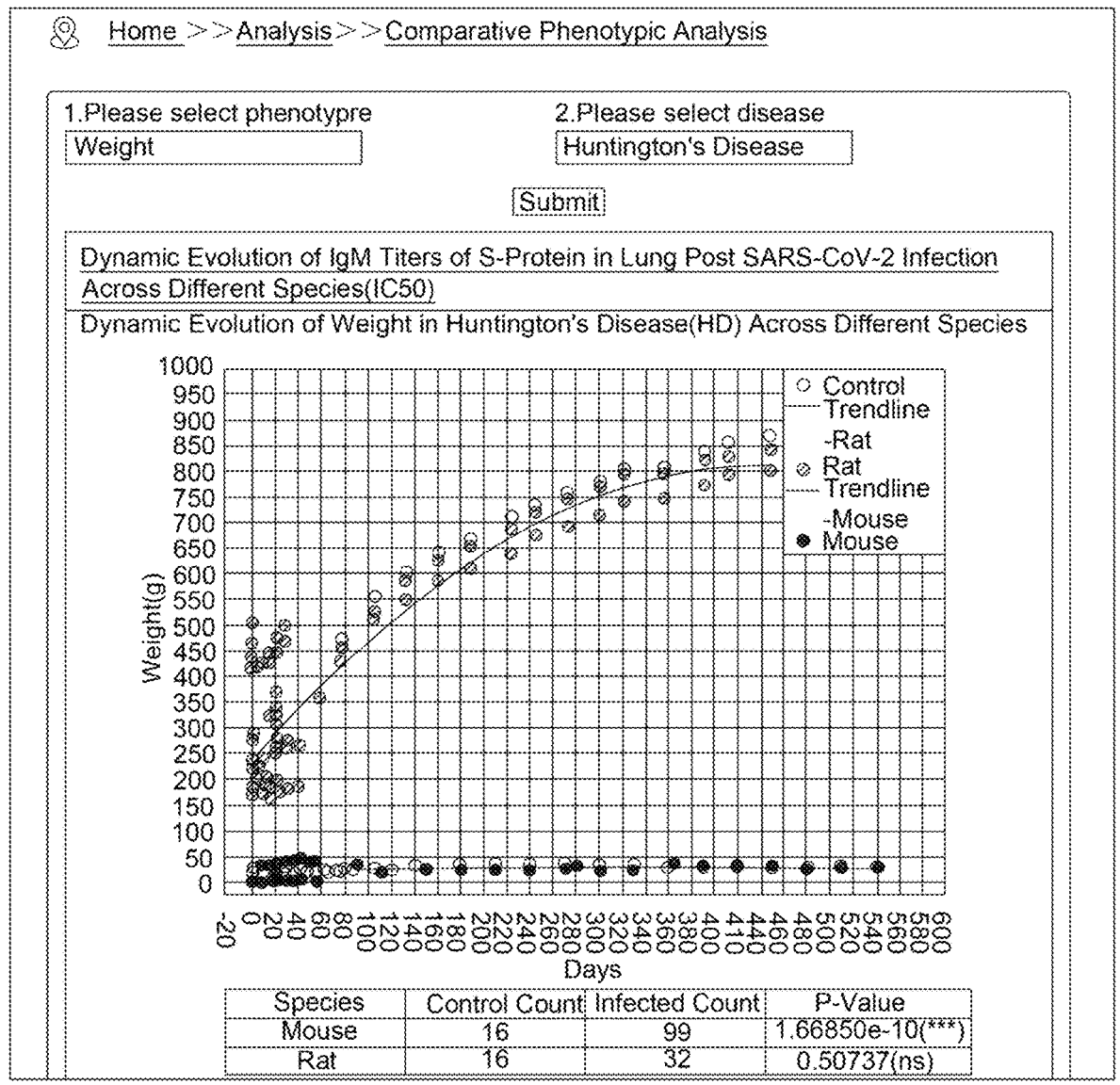
FIG. 10 is a schematic diagram showing a comparative analysis result of weights of different species according to Embodiment 1 of the present disclosure.
Figure 11:
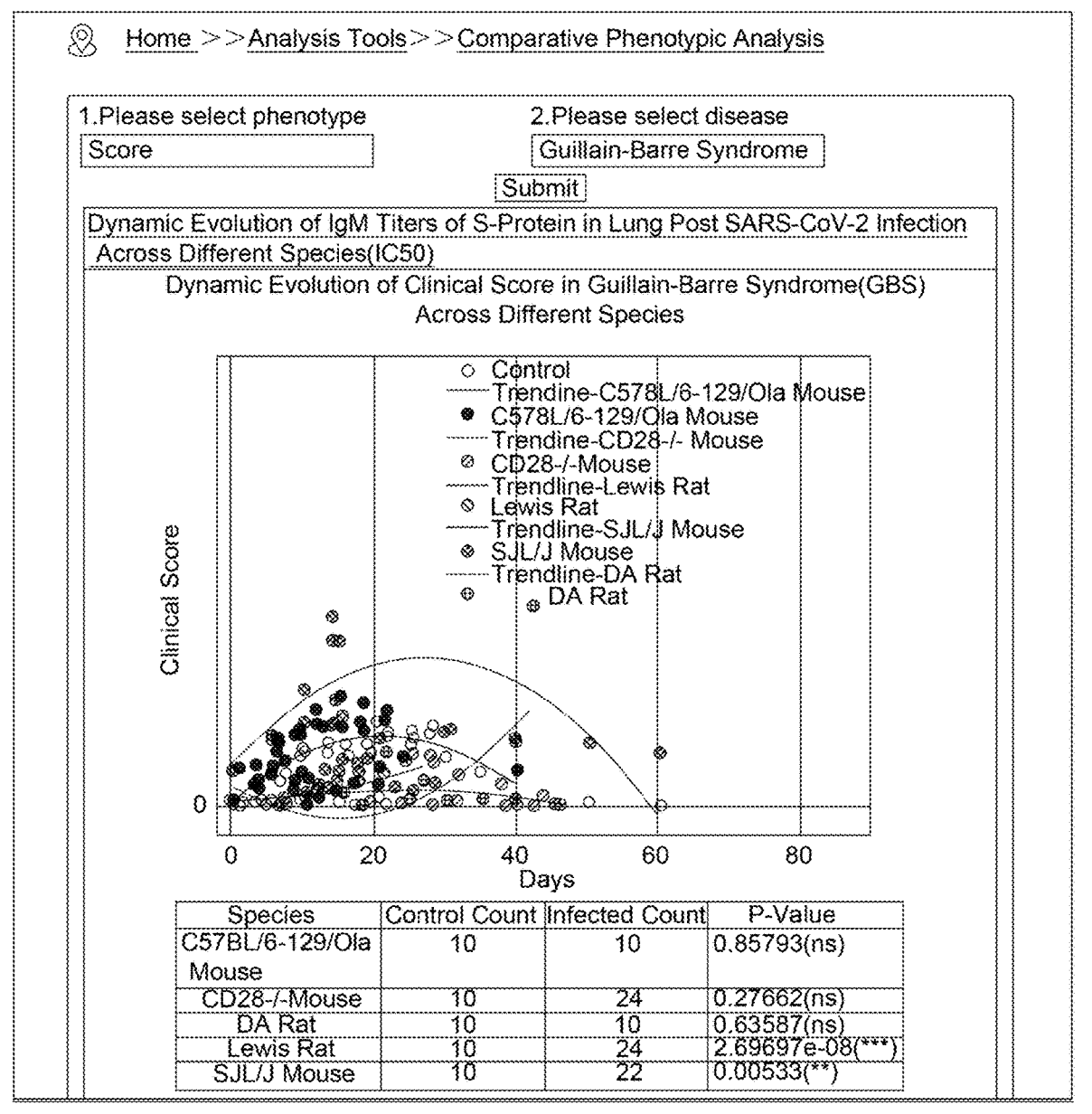
Figure 12:
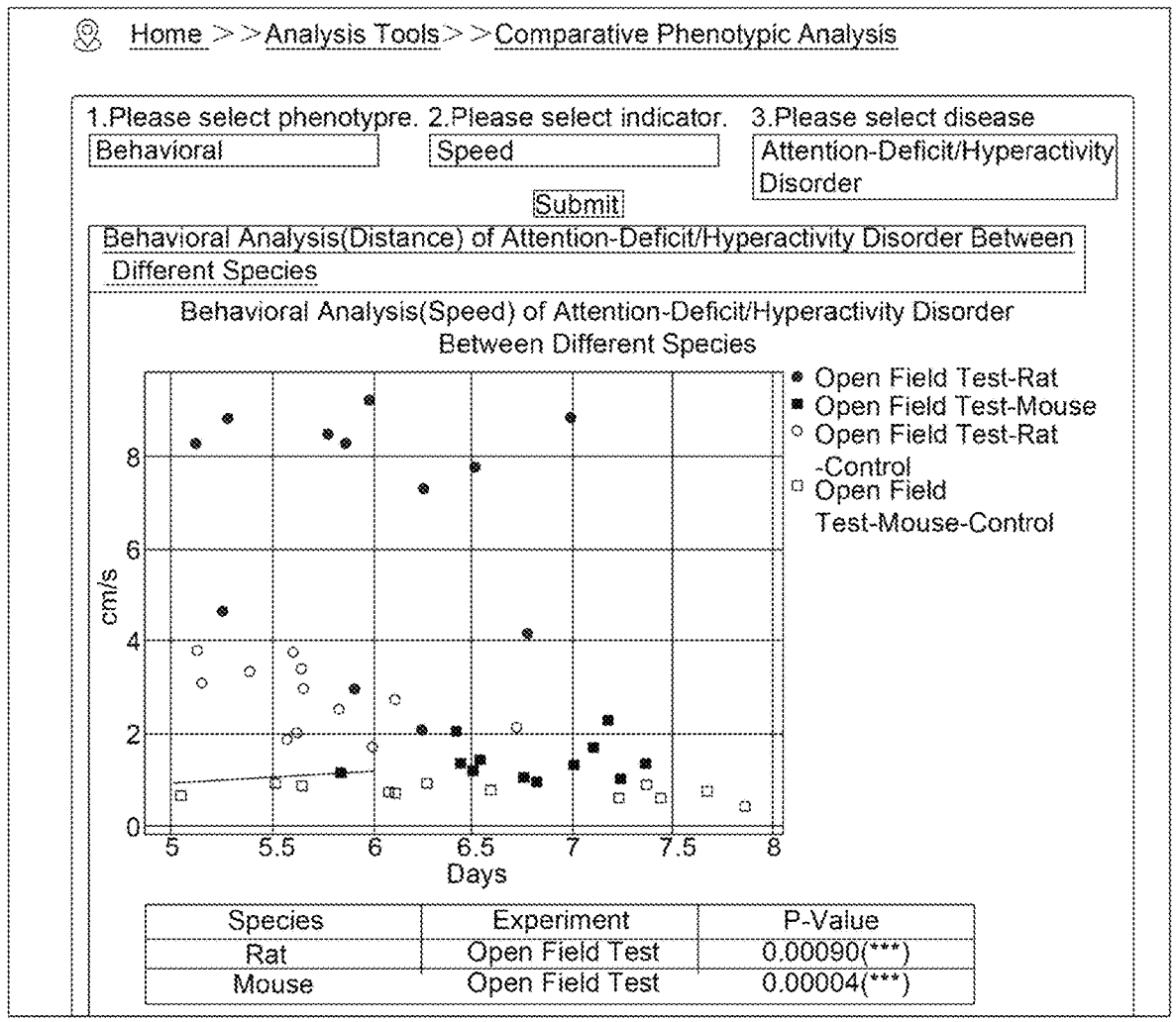
FIG. 12 is a schematic diagram showing a comparative analysis result of behavior of different species according to Embodiment 1 of the present disclosure.

Specifically, the user first selects a kind of phenotypic data (behavior, clinical scores, weights, or survival rates) for comparative analysis, and then selects a nervous system disease and species (multiple choices are allowed). After submission, a comparative analysis chart and a corresponding data table (including a p value) are displayed interactively. The database invokes corresponding data according to the user's choice, and uses exploratory data analysis (EDA) to clean the data based on Numpy and Pandas of Python, including missing value dealing, duplicate value dealing, data type conversion, data screening, and the like, and encapsulates the data into a method for comparative analysis. Matplotlib and Seaborn of Python are used to draw visual images such as a histogram, a box plot, and a scatter diagram respectively by means of corresponding modules. Interactive diagrams are drawn by means of Plotly (v 1.5.10), and corresponding HyperText Markup Language (HTML) pages are generated by means of JavaScript and cascading style sheets (CSS). Comparative analysis results of weights of different species suffering from Huntington's disease are shown in FIG. 10. Clinical scores of Guillain-Barré Syndrome of different species are shown in FIG. 11. Comparative analysis results of behavioral phenotypic data of different species are shown in FIG. 12.

A model recommendation process is as follows:

determining a recommended model based on a user input instruction and the animal model database, which specifically includes: querying from the animal model database based on a key field in the user input instruction to obtain application data with occurrence frequencies ranking in a descending order and whose quantity is a set value; and forming the recommended model by all the application data with occurrence frequencies ranking in a descending order and whose quantity is the set value. The set value is 20.

The user sequentially selects a disease type, a disease name and a research purpose (phenotype and symptom comparison, mechanism research, gene function research, gene tracing, behavioral research, pathological research, human disease research, drug screening and efficacy evaluation) that the user wants to study, and after submission, a model is recommended based on "model application" and "frequency of model appearance". A list of models, including model names, numbers, and corresponding literature, is displayed. Model recommendation results are shown in FIG. 13. For example, after the user selects "Neurodegenerative Diseases", disease options are correspondingly changed to Neurodegenerative Diseases (Alzheimer's Disease, Parkinson's Disease, Huntington's Disease, and the like) contained in the database, and the user selects a disease of interest (for example, "Alzheimer's disease"), and may select one or more research purposes (for example, "Mechanistic Investigation"). A list of the most commonly used Alzheimer's disease models for mechanism research is recommended, and clicking on a model number can open a detail page of a corresponding animal model of neurological diseases.

Recommendation rules are as follows: models in each piece of literature are split according to elements contained in naming rules. A model is recommended according to the naming rules and the application of animal models of neurological diseases. The model is defined as including a disease type, a disease name and a use, and all the names are standardized and unified, for example, Alzheimer's disease, AD, Alzheimer, and the like are unified as Alzheimer's disease. Therefore, after the user selects the disease type, the disease name and the research purpose (model application information) online, a list of corresponding model names is called up according to the fields of "disease type", "disease name" and "application" defined in each model name. If a model appears many times, the model is often used by researchers, thereby providing guidance for the user to choose the model during a subsequent experimental design.

The naming rules of names are illustrated with induced animal models, genetically engineered animal models, and induced and genetically edited animal models as examples.

1. Induced Animal Models:
    Naming rules: XX (reagent) induced+strain+species+disease name+model.
    For example: 6-hydroxydopamine (OHDA) induced SD rate Parkinson's disease model. 1-methyl-4-phenyl-1,2,3,6-tetrahydropyridine (MPTP) induced Cynomolgus monkey Parkinson's disease model.
2. Genetically Engineered Animal Models:
    Naming rules: Gene name+transgenic+strain+species+disease+model.
    For example: APP/PS1 transgenic C57BL/6J mouse Alzheimer's disease model.
3. Induced and Genetically Edited Animal Models:
    Naming rules: XX (reagent) induced+strain (including name of transgene-name of background strain)+species+disease name+model.

In this implementation, models, phenotypes, applications and related data are extracted through supplementary collection of literature and public databases. The data is preprocessed, integrated, analyzed, and visualized to establish a database of animal models of neurological diseases, and comparative analysis and model recommendation tools are developed based on the models, the phenotypes, and application data. The mode of Internet+disease model is adopted to integrate scattered information of animal models of neurological diseases and build a network platform. Different models and experimental data such as physiological and biochemical data, molecular pathological data, immune data, and image data after medication are integrated. Data modeling and exploratory data analysis are used for analysis. Various methods such as data modeling and exploratory data analysis are adopted for analysis, and visual tools are adopted for display. Application data of a total of 480 models and related model is integrated. This takes the lead in creating online comparative analysis and model recommendation functions, forming systematic integration, storage and mining of data. The database of animal models of neurological diseases is built for the first time to implement data integration, sharing and comparative analysis.

The present application further provides an application scenario, and the method for recommendation and comparative analysis of an animal model of neurological diseases is applied in the application scenario. Specifically, the method for recommendation and comparative analysis of an animal model of neurological diseases according to this embodiment can be applied in an experimental scenario of drug testing for neurological diseases. Related literature on animal models of neurological diseases is obtained. From a data acquisition link to a literature data processing link, information is extracted from the related literature on animal models of neurological diseases to obtain literature information of the related literature on animal models of neurological diseases. The literature information is preprocessed to obtain phenotypes and application data corresponding to related literature on animal models of neurological diseases. An animal model database is constructed based on phenotypes and application data corresponding to all the related literature on animal models of neurological diseases, and then a recommended model is determined based on a user instruction and the animal model database. The user optimizes the experimental process of drug testing based on the recommended model, and performs comparative analysis on the phenotypes corresponding to the related literature on animal models of neurological diseases based on a user input phenotype instruction to obtain a comparative analysis result. Based on the comparative analysis result, the experimental process of drug testing is optimized. The method for recommendation and comparative analysis of an animal model of neurological diseases according to this embodiment is a literature data processing link.

The integration of the phenotype and the application data of the animal models and the construction and opening and utilization of the database can solve the problem of scattered data, help shorten an experimental period, improve experimental efficiency, avoid repeated research, and conform to the rules of 3R. Researchers may optimize the experiment according to the existing experimental scheme design and experimental indexes in the database, such as selecting appropriate laboratory animal species and strains, age, gender, specifications, and quality standards, adopt an appropriate grouping method, and select scientific and reliable detection technical indexes, and the like, so as to optimize the experimental scheme and find a suitable animal model. In addition, by the network platform, the sharing of laboratory animal resources, animal models and phenotypic information is promoted. The method is applied to the research of a nervous system disease mechanism, provides data support, promotes comparative medical research, and can significantly improve research efficiency.

This embodiment has the following beneficial effects.

1) Models, phenotypes and application data are integrated. The data is subjected to quality control and standardization and is display by the network platform. A database of animal models of neurological diseases is established, to provide a series of data from the models and the phenotypes to the applications.
2) Similarities and differences between patients with neurological diseases and animal models are compared from the phenotypic level, to establish an intra-species and cross-species comparative analysis technology, and the data is visualized by means of this technology, thereby implementing multi-angle and multi-level comparative analysis, and solving the problem of cross-species comparison.
3) The database of animal models of neurological diseases is established to implement storage and display of animal models, phenotypes, application evaluation and other information, so as to provide convenient, fast and visualized valid data to the user, and implement a new paradigm of dynamic, multi-scale and multi-dimensional panoramic research. According to existing experimental schemes in the database, researchers may choose scientific and reliable detection technical indexes to optimize the experimental schemes. A comparative analysis function implements changes of different phenotypic indexes in different species and different diseases and displays the changes interactively. The model recommendation function can provide the most commonly used models according to the user's research needs, and allow model details to be viewed.
4) By regular update of website literature and model information, the content and structure of a website are constantly optimized, and a good internal link structure and an external link strategy are maintained to ensure a fast loading speed of the website, so as to attract the user for continuous access. With a simple and clear layout, a clear navigation menu and an easy-to-use retrieval system, the user can easily find information needed, improve user stickiness with high-quality, unique and valuable content and functions, and exchange friendly links with relevant websites in the industry (the comparative medicine big-data platform, National Human Disease Animal Model Resource Center, the National Animal Model Resource Sharing Information Platform, and the animal model drug screen database, and the like) to expand the promotion effect.

Embodiment 2

To perform the method corresponding to Embodiment 1 and achieve corresponding functions and technical effects, a system for recommendation and comparative analysis of an animal model of neurological diseases is provided below, including a terminal 102 and a server 104.

The terminal 102 is configured to obtain a plurality of pieces of related literature on animal models of neurological diseases.

The server 104 includes an information extraction module, an animal model database construction module, a model recommendation module, and a comparative analysis module.

The information extraction module is configured to extract, for each piece of related literature on animal models of neurological diseases, information from the related literature on animal models of neurological diseases to obtain literature information of the related literature on animal models of neurological diseases, the literature information including a model summary, a modeling strain, a modeling method, and phenotypic information, and the phenotypic information including clinical indexes, and behavioral, physiological and biochemical, pathological and image data.

The animal model database construction module is configured to preprocess the literature information to obtain phenotypes and application data corresponding to the related literature on animal models of neurological diseases, and construct an animal model database based on phenotypes and application data corresponding to all the related literature on animal models of neurological diseases.

The model recommendation module is configured to determine a recommended model based on a user input instruction and the animal model database, the recommended model being configured to optimize an experimental process of drug testing for neurological diseases, the user input instruction including a disease type, a disease name, and a use, and the recommended model including the application data corresponding to the related literature on animal models of neurological diseases.

The comparative analysis module is configured to perform comparative analysis on the phenotypes corresponding to the related literature on animal models of neurological diseases by the server based on a user input phenotype instruction to obtain a comparative analysis result, the comparative analysis result being used to optimize the experimental process of drug testing for neurological diseases, and the user input phenotype instruction being a plurality of phenotypic types required by a user.

Figure 14:
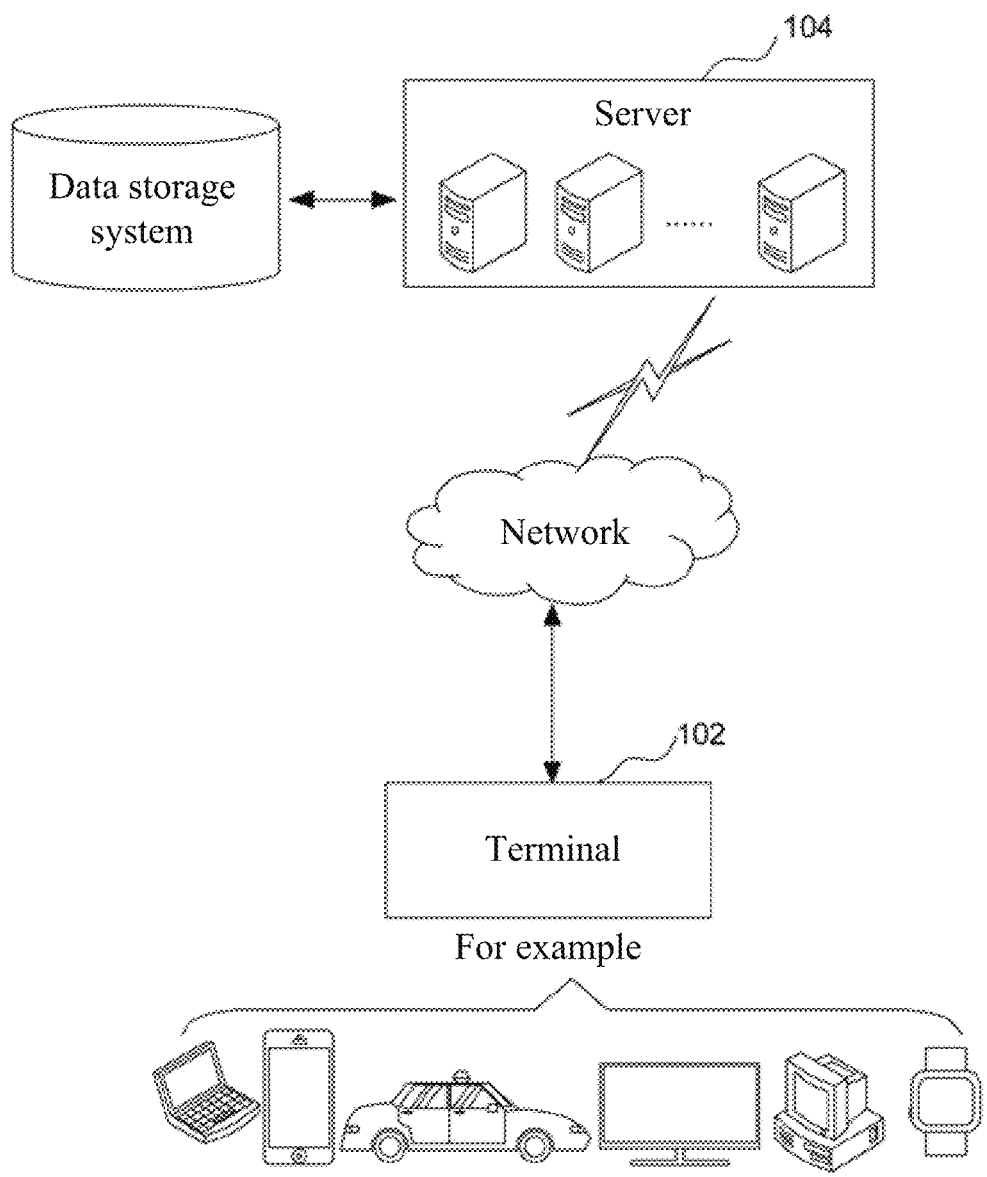
FIG. 14 is a schematic structural diagram of a system for recommendation and comparative analysis of an animal model of neurological diseases according to an embodiment of the present disclosure.

The method for recommendation and comparative analysis of an animal model of neurological diseases according to the embodiment of the present disclosure can be applied to the system shown in FIG. 14. The terminal 102 is in communication with the server 104 via a network. A data storage system can store data that the server 104 needs to process. The data storage system may be arranged separately, or integrated on the server 104, or placed on cloud or another server. The terminal 102 may send related literature on animal models for neurological diseases to the server 104. After the server 104 receives the related literature on animal models for neurological diseases, the server 104 performs data processing and information extraction on the related literature on animal models for neurological diseases to obtain phenotypes and application data corresponding to the related literature, and constructs an animal model database based on the phenotypes and the application data corresponding to the related literature, and the user can determine a recommended model by means of the animal model database. The server 104 further performs comparative analysis on the phenotypes corresponding to the related literature on animal models for neurological diseases. The server 104 may feed back the obtained recommended model and the comparative analysis result to the terminal 102. In addition, in some embodiments, the method for recommendation and comparative analysis of an animal model of neurological diseases may alternatively be implemented by the server 104 or the terminal 102 alone. For example, the terminal 102 may directly perform data processing on the to-be-processed related literature on animal models of neurological diseases, or the server 104 may obtain the to-be-processed related literature on animal models of neurological diseases from the data storage system and perform data processing on the to-be-processed related literature on animal models of neurological diseases.

The terminal 102 may be, but is not limited to, various desktop computers, laptops, smartphones, and tablets. The server 104 may be implemented by an independent server or a server cluster including a plurality of servers, or may be a cloud server.

Embodiment 3

A computer apparatus includes a memory, a processor, and a computer program stored in the memory and executable on the processor, and the processor executes the computer program to implement the steps of the method for recommendation and comparative analysis of an animal model of neurological diseases in Embodiment 1.

Embodiment 4

A computer-readable storage medium stores a computer program thereon, and when the computer program is executed by a processor, the steps of the method for recommendation and comparative analysis of an animal model of neurological diseases in Embodiment 1 are implemented.

Embodiment 5

A computer program product includes a computer program, and when the computer program is executed by a processor, the steps of the method for recommendation and comparative analysis of an animal model of neurological diseases in Embodiment 1 are implemented.

Embodiment 6

A computer device is provided, and the computer device may be a database. The computer device includes a processor, a memory, an input/output (I/O) interface, and a communication interface. The processor, the memory and the input/output interface are connected by a system bus, and the communication interface is connected to the system bus by the input/output interface. The processor of the computer device is configured to provide computing and control capabilities. The memory of the computer device includes a nonvolatile storage medium and an internal memory. The nonvolatile storage medium stores an operating system, a computer program, and a database. The internal memory provides an environment for operation of the operating system and the computer program in the nonvolatile storage medium. The database of the computer device is configured to store pending transactions. The input/output interface of the computer device is configured to exchange information between the processor and an external device. The network interface of the computer device is configured to communicate with an external terminal through a network connection. When the computer program is executed by the processor, the method for recommendation and comparative analysis of an animal model of neurological diseases in Embodiment 1 is implemented.

It should be noted that object information (including but not limited to object device information and object personal information) and data (including but not limited to data for analysis, stored data, and displayed data) involved in the present disclosure are all information and data authorized by an object or fully authorized by all parties, and the collection, use and processing of relevant data need to comply with relevant laws, regulations and standards of relevant countries and regions.

Those of ordinary skill in the art may understand that all or some of the processes in the method of the foregoing embodiments may be completed by a computer program instructing related hardware. The computer program may be stored in a nonvolatile computer-readable storage medium. The computer program, when executed, may include processes of the embodiment of each of the methods described above. Any reference to a memory, a database, or other media used in each embodiment of the present disclosure may include at least one of a nonvolatile memory and a volatile memory. The nonvolatile memory may include a read-only memory (ROM), a magnetic tape, a floppy disk, a flash memory, an optical memory, a high-density embedded nonvolatile memory, a resistive random access memory (ReRAM), a magnetoresistive random access memory (MRAM), a ferroelectric random access memory (FRAM), a phase change memory (PCM), a graphene memory, and the like. The volatile memory may include a random access memory (RAM) or an external cache memory, or the like. As an illustration rather than a limitation, the RAM may be in various forms, such as a static random access memory (SRAM) or a dynamic random access memory (DRAM). The database involved in each embodiment of the present disclosure may include at least one of a relational database and a non-relational database. The non-relational database may include a blockchain-based distributed database, and the like, but is not limited thereto. The processor involved in each embodiment of the present disclosure may be a general-purpose processor, a central processing unit, a graphics processor, a digital signal processor, a programmable logic device, a data processing logic device based on quantum computing, and the like, but is not limited thereto.

The technical features of the above embodiments can be arbitrarily combined. To make the description concise, none of all possible combinations of the technical features in the above embodiments are described. However, provided that no contradiction occurs between the combinations of these technical features, the combinations should be considered as falling within the scope of this specification.

Particular examples are used herein for illustration of principles and implementations of the present disclosure. The descriptions of the above embodiments are merely used for assisting in understanding the method of the present disclosure and its core ideas. In addition, those of ordinary skill in the art can make changes in terms of specific implementations and the scope of application in accordance with the ideas of the present disclosure. In conclusion, the content of this specification shall not be construed as limitations to the present disclosure.

What is claimed is:

1. A method for recommendation and comparative analysis of an animal model of neurological diseases, comprising:
obtaining a plurality of pieces of related literature on animal models of neurological diseases by a terminal;
extracting, for each piece of related literature on animal models of neurological diseases, information from the related literature on animal models of neurological diseases by a server to obtain literature information of the related literature on animal models of neurological diseases, the literature information comprising a model summary, a modeling strain, a modeling method, and phenotypic information, and the phenotypic information comprising clinical indexes, and behavioral, physiological and biochemical, pathological and image data;

preprocessing the literature information by the server to obtain phenotypes and application data corresponding to the related literature on animal models of neurological diseases, and constructing an animal model database based on phenotypes and application data corresponding to all the related literature on animal models of neurological diseases;

determining a recommended model by the server based on a user input instruction and the animal model database, the recommended model being configured to optimize an experimental process of drug testing for neurological diseases, the user input instruction comprising a disease type, a disease name, and a use, and the recommended model comprising the application data corresponding to the related literature on animal models of neurological diseases; and performing comparative analysis on the phenotypes corresponding to the related literature on animal models of neurological diseases by the server based on a user input phenotype instruction to obtain a comparative analysis result, the comparative analysis result being used to optimize the experimental process of drug testing for neurological diseases, and the user input phenotype instruction being a plurality of phenotypic types required by a user, wherein obtaining the plurality of pieces of related literature on animal models of neurological diseases by the terminal comprises:

employing a comprehensive search strategy across multiple databases for retrieval of pertinent literature by utilizing compound search formulas which combines neurological disease names with animal model species to retrieve and download literature, wherein standard neurological diseases names are compiled and keyword lists and catalogs for search are established;

giving priority to reviewing recent reviews;

establishing inclusion criteria according to documentation of neurological animal models with transparent animal backgrounds, modeling methods, and designs for testing a reliability and validity of models;

wherein constructing the animal model database comprises:

constructing a basic structure, style, and interactive functionalities of a web;

using Python for handling the web's business logic and data transmission;

adopting a structure of backend and a middleware, and employing a relational database for storing and managing structured data;

building a static file server, and performing load balancing and reverse proxy.

2. The method for recommendation and comparative analysis of an animal model of neurological diseases according to claim 1, wherein the preprocessing comprises: type conversion, deletion of duplicate lines, and missing value handling.

3. The method for recommendation and comparative analysis of an animal model of neurological diseases according to claim 1, wherein the extracting information from the related literature on animal models of neurological diseases specifically comprises:

extracting information from the related literature on animal models of neurological diseases by means of a Data Thief tool.

4. The method for recommendation and comparative analysis of an animal model of neurological diseases according to claim 1, wherein the performing comparative analysis on the phenotypes corresponding to the related literature on animal models of neurological diseases based on a user input phenotype instruction to obtain a comparative analysis result specifically comprises:

performing comparative analysis on phenotypic data corresponding to each piece of related literature on animal models of neurological diseases in the animal model database based on the user input phenotype instruction and a sample size in the phenotypic data, to obtain a descriptive data graph and a trend line, the descriptive data graph and the trend line forming the comparative analysis result.

5. The method for recommendation and comparative analysis of an animal model of neurological diseases according to claim 1, wherein the determining a recommended model based on a user input instruction and the animal model database specifically comprises:

querying from the animal model database based on a key field in the user input instruction to obtain a set number of application data with occurrence frequencies ranking in a descending order; and forming the recommended model by the set number of application data with occurrence frequencies ranking in a descending order, the key field comprising a disease type, a disease name, and a use.

6. The method for recommendation and comparative analysis of an animal model of neurological diseases according to claim 5, wherein the set number is 20.

7. The method for recommendation and comparative analysis of an animal model of neurological diseases according to claim 1, wherein after the constructing an animal model database, the method further comprises:

visually displaying data in the animal model database.

* * * * *